United States Patent
Zeng et al.

(10) Patent No.: US 9,789,033 B2
(45) Date of Patent: Oct. 17, 2017

(54) POLYACRYLATE OIL GEL AND METHODS

(71) Applicant: Rohm and Haas Company, Philadelphia, PA (US)

(72) Inventors: Fanwen Zeng, Belle Mead, NJ (US); Ying O'Connor, Coatesville, PA (US); Xiaodong Lu, North Wales, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/897,267

(22) PCT Filed: Jun. 17, 2014

(86) PCT No.: PCT/US2014/042699
§ 371 (c)(1),
(2) Date: Dec. 10, 2015

(87) PCT Pub. No.: WO2014/204937
PCT Pub. Date: Dec. 24, 2014

(65) Prior Publication Data
US 2016/0128914 A1 May 12, 2016

Related U.S. Application Data

(60) Provisional application No. 61/837,880, filed on Jun. 21, 2013.

(51) Int. Cl.
| | |
|---|---|
| *A61K 8/04* | (2006.01) |
| *A61K 8/37* | (2006.01) |
| *A61Q 19/00* | (2006.01) |
| *A61K 8/81* | (2006.01) |
| *A61K 8/58* | (2006.01) |
| *A61K 8/89* | (2006.01) |
| *A61K 8/92* | (2006.01) |
| *C08F 220/68* | (2006.01) |

(52) U.S. Cl.
CPC .............. *A61K 8/042* (2013.01); *A61K 8/375* (2013.01); *A61K 8/585* (2013.01); *A61K 8/8152* (2013.01); *A61K 8/89* (2013.01); *A61K 8/92* (2013.01); *A61Q 19/00* (2013.01); *A61Q 19/007* (2013.01); *C08F 220/68* (2013.01); *A61K 2800/84* (2013.01)

(58) Field of Classification Search
CPC .... A61K 8/375; A61K 8/585; A61K 2800/84; A61Q 19/00; C08F 220/68
USPC .......................................... 424/78.02; 514/221
See application file for complete search history.

(56) References Cited

U.S. PATENT DOCUMENTS

| | | | |
|---|---|---|---|
| 4,897,462 A | 1/1990 | Yusa et al. | |
| 2007/0286833 A1* | 12/2007 | Keller | A61K 8/8152 424/70.11 |
| 2010/0129303 A1* | 5/2010 | Dueva-Koganov | A61K 8/29 424/60 |
| 2013/0183361 A1* | 7/2013 | Tamareselvy | A61K 8/8152 424/401 |

FOREIGN PATENT DOCUMENTS

| | | |
|---|---|---|
| EP | 1273286 A2 | 1/2003 |
| WO | 2010/043588 A1 | 4/2010 |
| WO | 2013095993 A2 | 6/2013 |

OTHER PUBLICATIONS

Hitachi, title: DSC MEasurement if Polystyrene—The effect of molecular weight on glass transition-; Application Brief, TA No. 68, published Aug. 1995.*

Hermsdorp, H; Saturated Triglycerides and Their Derivatives in Cosmetic Creams and Lotions; Cosmetics & Toiletries, Wheaton, IL, US; vol. 95, Apr. 1, 1988, pp. 61-63.

Alexander, P.; Reconstituted Triglycerides and Their Use in Cosmetic Applications; SPC-Soap, Perfumery & Cosmetics; vol. 69, No. 11, Nov. 1, 1987, pp. 48-50.

* cited by examiner

*Primary Examiner* — Yanzhi Zhang
(74) *Attorney, Agent, or Firm* — Edward L. Brant

(57) ABSTRACT

Described are personal care compositions comprising a polyacrylate oil gel, comprising: (a) at least one cosmetically acceptable hydrophobic ester oil, and (b) one or more polymers comprising: (i) a first polymerized unit, comprising: (1) 75% to 35% by weight, based on the weight of said polymerized unit, one or more (meth)acrylate monomers selected from at least one of C1-C4 (meth)acrylate, (meth) acrylic acid, styrene, or substituted styrene, and (2) 25% to 65% by weight, based on the weight of said polymerized unit, one or more hydrophobic monomers, including hydrophobically substituted (meth)acrylate monomers, with alkyl chain length from C6 to C22 and, (ii) a second polymerized unit, comprising: (1) 10-99% by weight, based on the weight of said polymerized unit, one or more monomers which has a Tg of more than 80° C. after polymer formation, (2) 1-10% of one or more (meth)acrylate monomers containing acid functional group, and (iii) optionally, a crosslinker.

14 Claims, No Drawings

POLYACRYLATE OIL GEL AND METHODS

FIELD

The present invention relates to compositions for improving sensory feel in personal care compositions.

BACKGROUND

Aesthetics are important considerations in skin care compositions. The need for leave-on skin compositions to impart good sensory feel is well known, but achieving a smooth, silky feel for such products is a challenge. Despite otherwise excellent functionality, consumers will not feel loyalty to any facial care, body care, hand cream, sunscreen, deodorant, or cosmetic with poor sensory performance.

Historically, the skin care art has developed sensory agents, such as silicone oils, hard particles (such as Poly (methyl methacrylate) (PMMA) particles and polyethylene (PE) particles), and silicone elastomer gels in order to impart good aesthetics. However, each of the foregoing is associated with certain drawbacks, like insufficient sensory performance, dry after-feel on skin, or relatively high cost.

Accordingly, what is needed are cost-effective high performance sensory agents, preferably with good stability and texture in skin care formulations.

DETAILED DESCRIPTION

In one embodiment, the present invention provides personal care compositions comprising a polyacrylate oil gel, comprising: (a) at least one cosmetically acceptable hydrophobic ester oil, and (b) one or more polymers comprising: (i) a first polymerized unit, comprising: (1) 75% to 35% by weight, based on the weight of said polymerized unit, one or more (meth)acrylate monomers selected from at least one of C1-C4 (meth)acrylate, (meth)acrylic acid, styrene, or substituted styrene, and (2) 25% to 65% by weight, based on the weight of said polymerized unit, one or more hydrophobic monomers, including hydrophobically substituted (meth) acrylate monomers, with alkyl chain length from C8 to C22 and, (ii) a second polymerized unit, comprising: (1) 10-99% by weight, based on the weight of said polymerized unit, one or more monomers which has a Tg of more than 80° C. after polymer formation, (2) 1-10% of one or more (meth)acrylate monomers containing acid functional group, and (iii) optionally, a crosslinker.

In one embodiment, the polyacrylate oil gel is used as a sensory agent or sensory modifier, to impart superior aesthetic feel to personal care compositions. Examples of personal care compositions in need of sensory modifiers include facial care, body care, hand cream, sunscreen, deodorant, or cosmetic compositions. Contemplated usage levels for the polyacrylate oil gel range from 0.5% to 10%, preferably 2% to 6%, more preferably 4% by weight of the personal care composition. In one embodiment, the pH of the personal care composition is between 5 and 7.

The polyacrylate oil gel comprises the polymers described below at range of 1% to 50% (by weight percentage) and oil.

As used herein, "(meth)acrylic" means acrylic or methacrylic; "(meth)acrylate" means acrylate or methacrylate; and "(meth)acrylamide" means acrylamide or methacrylamide. "Substituted" means having at least one attached chemical group such as, for example, alkyl group, alkenyl group, vinyl group, hydroxyl group, carboxylic acid group, other functional groups, and combinations thereof.

Styrene and substituted Styrene monomers have one ethylenically unsaturated group per molecule. Examples of Styrene and substituted Styrene monomers include 4-methylstyrene, 2-methylstyrene, 3-methylstyrene, 4-methoxystyrene, 2-hydroxymethylstyrene, 4-ethylstyrene, 4-ethoxystyrene, 3,4-dimethylstyrene, 2-chlorostyrene, 3-chlorostyrene, 4-chloro-3-methylstyrene, 4-t-butylstyrene, 2,4-dichlorostyrene, 2,6-dichlorostyrene. Preferred Styrene and substituted Styrene monomers include styrene (Sty) and 4-methylstyrene (vinyltoluene).

Preferred (meth)acrylate monomer containing acid functional group include acrylic acid, methacrylic acid, itaconic acid, crotonic acid. More preferred (meth)acrylate monomers containing acid functional group are acrylic acid, methacrylic acid.

Cosmetically Acceptable Hydrophobic Ester Oil

In one embodiment, the cosmetically acceptable hydrophobic ester oil is caprylic/capric triglyceride. In one embodiment, the cosmetically acceptable hydrophobic ester oil is diffused in an oil base. A suitable oil base includes any oil or mixture of oils which are conventionally used in the personal care products. Examples include saturated fatty esters and diesters, such as isopropyl palmitate, octyl palmitate, butyl stearate, isocetyl stearate, octadodecyl stearoyl stearate, diisopropyl adipate, dioctyl sebacate, paraffin oils, paraffin waxes, animal oils and vegetable oils such as mink oil, coconut oil, soybean oil, palm oil, corn oil, cocoa butter, sesame oil, sunflower oil, jojoba oil, olive oil, lanolin oil, fatty alcohols such as stearyl alcohol, isostearyl alcohol, isocetyl alcohol. The oils listed are merely examples are not intended to limit the invention in any way. In general, any hydrophobic material or mixtures thereof which are toxicologically safe for human or animal use may constitute the oil base of the present invention.

Two-Stage Polymer

Polymers usefully employed according to the invention can be prepared by conventional emulsion, solution or suspension polymerization. Emulsion polymerization is preferred. Monomers used to prepare the polymers are added in a sequential process or randomly to afford non-random or random polymers using a free-radical initiator such as peroxygen compounds or diazo compounds and, optionally, chain transfer agents. The length of the primary polymer chains is typically such that, if any crosslinks were removed, the molecular weight (Mw) would be in the range of about 50,000 to 10,000,000, alternatively from 100,000 to 5,000,000, alternatively from 200,000 to 2,000,000.

A free radical initiator is utilized in solution and emulsion polymerizations. Suitable free radical initiators include hydrogen peroxide; tert-butyl hydroperoxide; sodium, potassium, lithium and ammonium persulfate and the like. A reducing agent, such as a bisulfite, including an alkali metal metabisulfite, hydrosulfite, and hyposulfite; and sodium formaldehyde sulfoxylate or a reducing sugar such as ascorbic acid or isoascorbic acid, may be used in combination with the initiator to form a redox system. Initiators usefully employed for suspension polymerization include oil soluble peroxides, hydroperoxides and azo compounds such as AIBN. The amount of initiator may be from 0.01% by weight to about 2% by weight of the monomer charged and in a redox system, a corresponding range of 0.01% by weight to about 2% by weight of reducing agent may be used. Transition metal catalysts, such as iron and copper salts, may be used.

The polymerization temperature may be in the range of about 10° C. to 120° C. in the aqueous emulsion, suspension and solution polymerizations. In the case of the persulfate systems, the temperature is preferably in the range of 60° C. to 90° C. In the redox system, the temperature is preferably in the range of 20° C. to 70° C.

For emulsion polymers, any emulsifiers or dispersing agents optionally employed for preparing the monomer emulsions or polymer emulsions may be anionic, cationic or nonionic types. Also a mixture of any two or more types may be used. Suitable nonionic emulsifiers include, but are not limited to, ethoxylated octylphenols, ethoxylated nonylphenols, ethoxylated fatty alcohols and the like. Suitable anionic emulsifiers include, but are not limited to, sodium lauryl sulfate, sodium dodecylbenzene sulfonate, sulfated and ethoxylated derivatives of nonylphenols, octylphenols and fatty alcohols, esterified sulfosuccinates and the like. Suitable cationic emulsifiers include, but are not limited to, laurylpyridinium chlorides, cetyldimethylamine acetate, ($C_8$-$C_{18}$) alkyldimethylbenzylammonium chlorides and the like. The level of emulsifier may be from about 0.1% to about 10% by weight, based on total monomer charged.

In one embodiment, the first polymerized unit (i) has a glass transition temperature ranging from −20° C. to 50° C. In one embodiment, monomer (1) is present in a range of 75% to 35% by weight of the first polymerized unit (i). Preferred monomers (1) are (meth)acrylate monomers with alkyl chain length of C4 and less. More preferred monomers (1) are butyl acrylate, ethyl acrylate, acrylic acid, methyl methacrylate, ethyl methacrylate, butyl methacrylate, and methacrylic acid.

In one embodiment, monomer (2) is present in a range of 25% to 65% by weight of the first polymerized unit (i). In one embodiment, monomer (2) is hydrophobically substituted (meth)acrylate monomers, with alkyl chain length from C6 to C22. Preferred monomers (2) are one or two monomer selected from ethylhexyl methacrylate, lauryl methacrylate, stearyl methacrylate, and cetyl-eicosyl methacrylate, behenyl methacrylate, ethylhexyl acrylate, lauryl acrylate, stearyl acrylate, cetyl-eicosyl acrylate, and behenyl acrylate. Most preferred monomers (2) are one or two monomer selected from ethylhexyl acrylate, lauryl methacrylate, and stearyl methacrylate.

In one embodiment, the second polymerized unit (ii) has a glass transition temperature ranging from 60-150° C. In one embodiment, the second polymerized unit (ii) comprises: (1) 10-99% by weight, based on the weight of said polymerized unit, one or more monomers which has a Tg of more than 80° C. after polymer formation, (2) 1-10% of one or more (meth)acrylate monomers containing acid functional group. In one embodiment, the second polymerized unit (ii) has a glass transition temperature higher than 80° C., for example, methyl methacrylate, tert-butyl methacrylate, styrene, and isoboryl methacrylate.

Polymers with high glass transition temperatures ("Tg") are typically used to lower the tackiness of polymer film properties. However, high Tg polymers have the drawback that they form films that are extremely hard and brittle. Preferably, the Tg of the second stage polymer is in the range of about 50 to 200° C., alternatively from 75 to 150° C., alternatively from 80 to 120° C.

In some embodiments of the invention, the stage 1 and stage 2 ratio is more than 50:50, preferably more than 60:40. In some embodiments of the invention, the stage 1 and stage 2 ratio is less than 99:1, preferably, less than 90 to 10.

In some embodiments, the first polymerized unit (i), a second polymerized unit (ii), or both, further comprise a cross-linker. Crosslinkers are monomers having two or more ethylenically unsaturated groups, and may include, e.g., divinylaromatic compounds, di-, tri- and tetra-(meth)acrylate esters, di-, tri- and tetra-allyl ether or ester compounds and allyl (meth)acrylate. Preferred examples of such monomers include divinylbenzene (DVB), trimethylolpropane diallyl ether, tetraallyl pentaerythritol, triallyl pentaerythritol, diallyl pentaerythritol, diallyl phthalate, diallyl maleate, triallyl cyanurate, Bisphenol A diallyl ether, allyl sucroses, methylene bisacrylamide, trimethylolpropane triacrylate, allyl methacrylate (ALMA), ethylene glycol dimethacrylate (EGDMA), hexane-1,6-diol diacrylate (HDDA) and butylene glycol dimethacrylate (BGDMA). Especially preferred crosslinkers include DVB, ALMA, EGDMA, HDDA and BGDMA. Most preferred crosslinker is ALMA. In some embodiments of the invention, the amount of polymerized crosslinker residue in the polymer is at least 0.01%, alternatively at least 0.02%, alternatively at least 0.05%. In some embodiments of the invention, the amount of crosslinker residue in the polymer is no more than 0.3%, alternatively no more than 0.2%, alternatively no more than 0.15%.

In one embodiment, the polyacrylate oil gel is combined with conventional sensory agents, such as silicone oils, hard particles (such as Poly(methyl methacrylate) (PMMA) particles and polyethylene (PE) particles), and silicone elastomer gels.

Silicones include silicone oils, for instance volatile or non-volatile polymethylsiloxanes (PDMS) comprising a linear or cyclic silicone chain, which are liquid or pasty at room temperature, especially cyclopolydimethylsiloxanes (cyclomethicones) such as cyclopentasiloxane and cyclohexadimethylsiloxane, polydimethylsiloxanes comprising alkyl, alkoxy or phenyl groups, which are pendent or at the end of a silicone chain, these groups comprising from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes 2-phenylethyltrimethyl siloxysilicates and polymethylphenylsiloxanes, fluoro oils such as partially hydrocarbon-based and/or partially silicone-based fluoro oils, preferably dimethicone, cyclopentasiloxane, cyclohexasiloxane, or a combination thereof. Preferably, the silicone is present in a range from about 0.1 wt % to about 5 wt %, preferably from about 0.75 wt % to about 3 wt %, and more preferably from about 1 wt % to about 2 wt %, by weight of the personal care composition.

In one embodiment, the present invention provides methods of making the polyacrylate oil gel, comprising: polymerizing the first polymerized unit (i) using emulsion polymerization, polymerizing the second polymerized unit (ii) using emulsion polymerization in the presence of the first polymerized unit (i), thereby forming polymer (b), isolating polymer b as a powder form, in one preferred embodiment, drying the polymer (b), and then adding the polymer (b) to the at least one cosmetically acceptable hydrophobic ester oil to form a polyacrylate oil gel. Powder forms of the polymer particles may be isolated from the aqueous dispersion in various ways, such as freeze-drying, spray-drying or coagulation. The techniques disclosed in U.S. Pat. No. 4,897,462, may also be applied to the polymer during isolation to produce a spheroidal product which, when dried, exhibits outstanding powder flow, low dusting, and higher bulk density than conventionally isolated powders.

In one embodiment, the inventive polyacrylate oil gel finds use in personal care products, preferably skin care, sun care, and hair care products. More specifically, the inventive polyacrylate oil gel finds use in sunscreens, skin lotions, cosmetics, skin lighteners, facial cleansers, body washes, shampoos, hair conditioners, and hair coloring products (i.e., 2-part hair dyes). In one embodiment, the inventive polyacrylate oil gel finds use as a sensory agent in such personal care products.

The following examples illustrate specific aspects and particular embodiments of the invention which, however, are not to be construed as limited thereby.

EXAMPLES

The following abbreviations are used in the Examples described herein:
BA=butyl acrylate
MAA=methacrylic acid
MMA=methyl methacrylate
EHA=ethylhexyl acrylate
ALMA=allyl methacrylate
CCT=caprylic/capric triglyceride Example 1

Two stage polymers useful in the present invention are listed in TABLE 1:

TABLE 1

| | Composition |
|---|---|
| Polymer 1 | Stage 1 (85%): 31 SMA/25 BA/29 STY/15 MAA<br>Stage 2 (15%): 99 MMA/1 MAA |
| Polymer 2 | Stage 1 (80%): 31 SMA/25 BA/29 STY/15 MAA<br>Stage 2 (20%): 99 MMA/1 MAA |
| Polymer 3 | Stage 1 (70%): 31 SMA/25 BA/29 STY/15 MAA<br>Stage 2 (30%): 99 MMA/1 MAA |
| Polymer 4 | Stage 1 (85%): 20 BA/40 EHA/38.5 MMA/1.5 MAA//0.075 ALMA<br>Stage 2 (15%): 99 MMA/1 MAA |
| Polymer 5 | Stage 1 (80%): 20 BA/40 EHA/38.5 MMA/1.5 MAA//0.075 ALMA<br>Stage 2 (20%): 99 MMA/1 MAA |
| Polymer 6 | Stage 1 (70%): 20 BA/40 EHA/38.5 MMA/1.5 MAA//0.075 ALMA<br>Stage 2 (30%): 99 MMA/1 MAA |
| Polymer 7 | Stage 1 (80%): 20 BA/40 EHA/38.5 MMA/1.5 MAA//0.075 ALMA<br>Stage 2 (20%): 99 MMA/1 MAA//0.075 ALMA |

A standard emulsion polymerization method is used. For example, for Polymer 7, 252 g of deionized water, 8 g of a 23% sodium dodecyl benzene sulfonate and 2 g of sodium carbonate are charged to a 2-liter round-bottom flask equipped with a overhead stirrer, thermocouple, condenser and inlets for the addition of monomer and initiators. The flask is stirred and heated to 92° C. A monomer emulsion (stage 1) is prepared by charging 146 g of deionized water and 5.6 g of sodium dodecyl benzene sulfonate (23%) to an appropriate container and set to stir. After the surfactant is incorporated into the water, 90 g of BA, 180 g of g of EHA, 174 g of MMA, 6.8 g of MAA, and 0.34 g of ALMA is added slowly to the stirring mixture. A cofeed catalyst solution is also prepared by charging 0.86 g of sodium persulfate and 50 g of deionized water.

At reaction temperature of 88° C., 19 g of the above prepared monomer emulsion is charged to the kettle with 5 g of deionized water rinse, followed by an initiator solution of 1.9 g sodium persulfate and 15 g water. After initial polymerization and at 85° C., the stage 1 monomer emulsion cofeed is begun at a rate of 4.72 g per minute for 15 minutes and 10.1 g per minute for 83 minutes. Simultaneously the stage 1 catalyst cofeed is begun at a rate of 0.61 g per minute for 88 minutes. At the completion of the monomer emulsion and catalyst cofeed, the reaction mixture is held for 10 minutes.

During the feed of stage 1, stage 2 monomer emulsion and catalyst are prepared. Stage 2 monomer emulsion is prepared by charging 52 g of deionized water and 2 g of sodium dodecyl benzene sulfonate (23%) to an appropriate container and set to stir. After the surfactant is incorporated into the water, 112 g of MMA, 1.1 g of g of MAA, and 0.09 g of ALMA is added slowly to the stirring mixture. A stage 2 cofeed catalyst solution is also prepared by charging 0.12 g of sodium persulfate and 14 g of deionized water. Upon the completion of stage 1 hold, the stage 2 monomer emulsion cofeed is begun at a rate of 6.55 g per minute for 29 minutes.

At the completion of the stage 2 monomer emulsion and catalyst cofeed, the reaction mixture is chased to reduce the amount of residual monomers. The resulting latex has the following characteristics.
Solids: 43.5%
Grit: <100 ppm
Mean Particle Size: 103 nm
Residual EHA: 29 ppm Polymers 3-8 are made substantially as described above, the appropriate changes being made.

Example 2

Polymers 4, 5, and 6 from Example 1 were frozen at −70° C. and then subjected to freeze drying with a bench-top lyophilizer (Labconco Freezer Dry System Lyph Lock®4.5). The appearance and texture of dried samples were observed by a trained panelist to have a loose structure and to be easy to break apart.

For comparison, a single stage Polymer A (20 BA/40 EHA/38.5 MMA/1.5 MAA//0.075 ALMA) was conventionally prepared, then frozen and then subjected to freeze drying with a bench-top lyophilizer as described above, and it yielded a gummy mass that was hard to break apart.

Example 3

Polymers 4, 5, and 6 from Example 2 were prepared as oil gels as follows. 12 grams dried polymer and 88 grams of CCT are placed in a glass container. The container is placed on a hot plate or a heat jack, preferably set up as a closed system with Nitrogen filled on top of the head space. Mixing with an overhead stirrer at a speed around 100-200 rpm, the batch is heated to about 70° C., and held at that temperature with mixing for 1 hour or until all the solids are dissolved. Additional heat up to 90° C. and/or mixing to 700 rpm are contemplated. The solution is allowed to cool to room temperature and is then evaluated. Polymers 4, 5, and 6 yielded smooth, thick, uniform solutions. Polymers 5 and 6 were flowable as well.

For comparison, a single stage Polymer A from Example 2 was prepared as above, but yielded a thin, hazy solution with big chunks and small gel-like particles floating in the solution, which is not acceptable for personal care sensory modifiers.

Example 4

To ascertain the advantages of the present invention as a sensory modifier, skin care lotions are prepared as listed in Table 2 (in %):

TABLE 2

|  | Batch 1 | Batch 2 | Comparative Batch A |
|---|---|---|---|
| Polymer 5 (12%) in CCT (Example 3) | 4 | 2 | — |
| DC 245 silicone oil | — | 2 | — |
| DC 9045 silicone elasotmer gel | — | — | 4 |
| Water | 82.7 | 82.7 | 82.7 |
| Glycerin | 2 | 2 | 2 |
| Xanthan gum | 0.7 | 0.7 | 0.7 |
| Cetearyl Alcohol (and) Ceteareth 20 | 3 | 3 | 3 |
| Glyceryl Stearate | 2 | 2 | 2 |
| Petrolatum | 5 | 5 | 5 |
| Neolone PE preservative | 0.6 | 0.6 | 0.6 |

In a vessel, add Xanthan gum into water, mix until dissolved; add Glycerin and mix while heating up to 75° C. to form a water phase. In a separate vessel, combine Cetearyl Alcohol (and) Ceteareth 20, Glyceryl Stearate, Petrolatum, and Polymer 5 (12%) in CCT (or/and DC245 Silicone Oil or DC9045 silicone elastomer gel), heat up to 75° C. while mixing until all components melt to form an oil phase. At 75° C., add the oil phase into the water phase with agitation, mix until a uniformed emulsion is generated. Turn off the heat, continue mix and air cool the batch to below 40° C.; add Neolone PE into the batch, mix well while cooling to room temperature. Compensate water loss by adding additional water and q.s. to 100% w/w. Adjust pH with Citric Acid (50% solution) to pH5-7 if necessary.

Example 5

To evaluate in-vivo sensory performance, 12 trained panelists each apply the compositions listed in Table 3, and then rate on a scale of 1-5 how undesirable (1) or desirable (5) the aesthetics are. 50 μl of each formulated sample (as listed in Table 2) was delivered by pipette or syringe onto 5 cm×5 cm pre-marked area located on panelist's forearm; the panelist then used his/her index or/and middle finger(s) to gently rub the sample in one direction (clockwise for example) within the pre-marked area, and evaluated each attribute by rating them on a scale from 1 (the least desirable) to 5 (the most desirable). The panelist evaluated Spreading, Oiliness, Waxiness, Tackiness and Absorption while rubbing the sample onto skin, and evaluated Smoothness while the sample dried on skin, usually 15 minutes after rubbing. The results are listed in TABLE 3.

TABLE 3

|  | Spreading | Oiliness | Waxiness | Tackiness | Absorption | Smoothness |
|---|---|---|---|---|---|---|
| Batch 1 | 4 | 3 | 3 | 5 | 4 | 4 |
| Batch 2 | 5 | 5 | 4 | 5 | 5 | 2 |
| Comparative Batch A | 5 | 4 | 5 | 5 | 5 | 5 |

The results show that the inventive Batch 1 compares favorably with the benchmark Comparative Batch A on tackiness, with close performance on spreading, absorption, and smoothness. Batch 2 compares favorably with the benchmark Comparative Batch A on spreading, tackiness, and absorption, with an even better performance on oiliness, which indicates that a synergistic sensory effect can be achieved by combining polyacrylate oil gel with silicone oil.

The invention claimed is:

1. A personal care composition comprising a polyacrylate oil gel, comprising:
    (a) at least one cosmetically acceptable hydrophobic ester oil, wherein the cosmetically acceptable hydrophobic ester oil is caprylic/capric triglyceride, and
    (b) one or more multistage polymers comprising:
        (i) a first stage polymerized unit, comprising:
            (1) 75% to 35% by weight, based on the weight of said first stage polymerized unit, one or more (meth)acrylate monomers selected from the group consisting of one of C1-C4 (meth)acrylate, (meth)acrylic acid, styrene, substituted styrene, and combinations thereof, and
            (2) 25% to 65% by weight, based on the weight of said first stage polymerized unit, one or more hydrophobic monomers selected from the group consisting of hydrophobically substituted (meth)acrylate monomers having an alkyl chain length from C6 to C22 and,
        (ii) a second stage polymerized unit, comprising:
            (1) 10-99% by weight, based on the weight of said second stage polymerized unit, one or more monomers selected from the group consisting of methyl methacrylate, tert-butyl methacrylate, styrene, isoboryl methacrylate, and combinations thereof,
            (2) 1-10% by weight, based on the weight of said second stage polymerized unit, one or more (meth)acrylate monomers containing acid functional group, and
        (iii) optionally, a crosslinker,
    wherein the one or more multistage polymers are prepared by emulsion polymerization.

2. The personal care composition of claim 1, wherein the first stage polymerized unit (i) has a glass transition temperature ranging from −20° C. to 50° C.

3. The personal care composition of claim 1, wherein monomer (1) of the first stage polymerized unit (i) is at least two of butyl acrylate, methyl methacrylate, methacrylic acid, or styrene.

4. The personal care composition of claim 1, wherein monomer (2) of the first stage polymerized unit (i) is at least one of ethylhexyl acrylate, lauryl methacrylate, stearyl methacrylate, and cetyl-eicosyl methacrylate, behenyl methacrylate, lauryl acrylate, stearyl acrylate, and cetyl-eicosyl acrylate, behenyl acrylate.

5. The personal care composition of claim 4, wherein monomer (2) of the first stage polymerized unit (i) is at least two of ethylhexyl acrylate, lauryl methacrylate, stearyl methacrylate, and cetyl-eicosyl methacrylate, behenyl methacrylate, lauryl acrylate, stearyl acrylate, and cetyl-eicosyl acrylate, behenyl acrylate.

6. The personal care composition of claim 1, wherein the second stage polymerized unit (ii) has a glass transition temperature ranging from 60–150° C.

7. The personal care composition of claim 1, wherein the pH of the personal care composition is between 5 and 7.

8. The personal care composition of claim 1, further comprising silicone oil, silicone elastomers, emollient, or hard particle sensory modifiers.

9. The personal care composition of claim 1, wherein the multistage polymer is a two stage polymer.

10. A method of making the polymer (b) of the polyacrylate oil gel of the personal care composition of claim 1, comprising
    forming the first polymerized unit (i) to form a first-stage polymer, and forming the second polymerized unit (ii) to form a second-stage polymer, and reacting the second-stage polymer with the first-stage polymer.

11. The personal care composition of claim 10, wherein the steps occur simultaneously, as a one kettle reaction.

12. The personal care composition of claim 10, wherein the ratio of first-stage polymer to second-stage polymer is in a range from 60:40 to 95:5.

13. A method of making the polyacrylate oil gel of the personal care composition of claim 1, comprising:

polymerizing the first polymerized unit (i) using emulsion polymerization, polymerizing the second polymerized unit (ii) using emulsion polymerization in the presence of the first polymerized unit (i), thereby forming polymer (b), drying the polymer (b), and then adding the polymer (b) to the at least one cosmetically acceptable hydrophobic ester oil to form a polyacrylate oil gel.

14. The method of claim 13, wherein the drying is freeze drying or spray drying.

* * * * *